(12) United States Patent
Travis et al.

(10) Patent No.: US 8,117,663 B2
(45) Date of Patent: *Feb. 14, 2012

(54) COMPUTERIZED METHOD AND SYSTEM FOR RESTRICTING ACCESS TO PATIENT PROTECTED HEALTH INFORMATION

(75) Inventors: John F. Travis, Kansas City, MO (US); Lori N. Cross, Kansas City, MO (US); Sarah L. Dahlhauser, Lee's Summit, MO (US); Stacy C. St. John, Kansas City, MO (US); James L. Stroud, Savannah, MO (US); Chandrasekhar K. Venkat, Shawnee, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 107 days.

This patent is subject to a terminal disclaimer.

(21) Appl. No.: 12/626,150

(22) Filed: Nov. 25, 2009

(65) Prior Publication Data

US 2010/0077487 A1 Mar. 25, 2010

Related U.S. Application Data

(63) Continuation of application No. 10/462,969, filed on Jun. 17, 2003, now Pat. No. 7,634,419.

(51) Int. Cl.
*G06F 7/04* (2006.01)
*H04N 7/16* (2011.01)

(52) U.S. Cl. .............................. 726/26; 713/182; 705/3
(58) Field of Classification Search .................. 726/26; 713/182; 705/3
See application file for complete search history.

(56) References Cited

U.S. PATENT DOCUMENTS

2002/0120472 A1* 8/2002 Dvorak et al. .................. 705/3
* cited by examiner

*Primary Examiner* — Christopher Brown
(74) *Attorney, Agent, or Firm* — Shook Hardy & Bacon LLP

(57) ABSTRACT

A computerized system and method for allowing restricted access to patient healthcare information is provided. Upon determining that one or more users are assigned to the location where an order for a patient is to be performed, the method allows one or more users restricted access to the order. The system includes an order entry module, an access evaluation module, a location entry module and a user module. The access evaluation module includes an assignment determination sub-module for determining whether one or more users are assigned to the specified location where an order for a patient is to be performed. The assignment determination module also includes a restricted access sub-module coupled with the assignment determination module and configured to allow restricted access to one or more users assigned to the specified location.

17 Claims, 3 Drawing Sheets

COMPUTERIZED METHOD AND SYSTEM FOR RESTRICTING ACCESS TO PATIENT PROTECTED HEALTH INFORMATION

CROSS-REFERENCE TO RELATED APPLICATIONS

This application is a continuation of U.S. Ser. No. 10/462,969, filed on Jun. 17, 2003.

STATEMENT REGARDING FEDERALLY THE SPONSORED RESEARCH OR DEVELOPMENT

Not applicable.

TECHNICAL FIELD

The present invention relates generally to the field of computer software. More particularly, the invention relates to a computerized system and method for restricting access to patient healthcare information.

BACKGROUND OF THE INVENTION

Patient healthcare records contain private information that patients often want to keep private from their employer, family, and the public. Examples of common types of sensitive health information that individuals have sought to keep private include HIV test results, drug testing results, and pregnancy test results. Historically, laboratories, individual laboratory departments and testing facilities of hospitals were operated locally. Patient information, if stored in a computerized environment, was stored in separate databases so that information was only available to those laboratory personnel/users with access to that particular database. Recently, hospitals, laboratories and healthcare organizations have begun storing patient information in integrated databases making the information available to a broad user base. The interconnectedness of patient information in these integrated databases increases the risk that sensitive healthcare information may be unnecessarily disclosed unless the information is properly secured with cognizance of the rights of laboratory personnel/users to access such healthcare information. Also, in an environment where multiple laboratories share a single information system, errors are more likely since a user may inadvertently select an order they are not authorized to access and enter test results for the wrong patient.

Recently, the Health Insurance Portability and Accountability Act (HIPAA) Privacy rule was enacted. HIPAA requires that covered entities, such as hospitals and clinics, take reasonable steps to limit the use or disclosure of protected health information. The policies and procedures of a covered entity must identify the persons (or classes of persons) within the covered entity who need access to protected health information to carry out their job duties, and the types of information needed for any given legitimate purpose. For example, laboratory technologists may only need access to certain portions of a patient's protected health information to carry out their job duties, and this access is only needed when the technologist is assigned work to be performed on behalf of the particular patient. Conversely, those persons involved in direct patient treatment, such as doctors or nurses, may need access to all of a patient's protected health information.

Currently, healthcare providers order particular procedures to be performed on a patient or on a sample obtained from a patient. These orders are input into the integrated database and assigned to a service location such as a laboratory or examination room. In many organizations, the same healthcare testing procedures may be performed at multiple service locations. A user typically is not assigned to all services locations where the test could be performed (i.e. all laboratories). As such, the user should not need access all service locations to perform his or her duty. Rather, the user should only be allowed access to those physical service locations relevant to his or her assigned duty, and to the relevant patient health information for those particular service locations.

Accordingly, there is a need for a system and method for restricting access to a patient's healthcare information at healthcare testing locations to prevent any unnecessary disclosure of patient health information.

SUMMARY OF THE INVENTION

The present invention prevents unauthorized disclosure of sensitive patient healthcare information and improves safety by reducing the likelihood that a user may enter results for a patient in the wrong order.

In one aspect of the invention, a method for allowing restricted access to a patient's healthcare information in a computing environment is provided. The method determines whether one or more users are assigned to the location where an order for a patient is to be performed. If so, the method allows one or more users restricted access to the order.

Another aspect of the invention is a computer system for allowing restricted access to patient healthcare information. The system includes an assignment determination module for determining whether one or more users are assigned to the specified location where an order for a patient is to be performed. The system further includes a restricted access module coupled with the assignment determination module. The assignment determination module is configured to allow restricted access to one or more users assigned to the specified location.

In yet another aspect of the present invention, a computerized system for allowing restricted access to patient health information is provided. The system includes means for determining whether one or more users are assigned to the specified location where an order for a patient is to be completed. The system also includes means for subsequently allowing the restricted access to the order if one or more users are assigned to the specified location.

In a further aspect of the present invention, one or more computer-readable media having a data structure stored thereon are provided. The data structure includes a first field containing data indicative of a healthcare related order to be performed at a specified location. The data structure includes a second field containing data indicative of the location assignment of one or more users so that restricted access may be granted to one or more users assigned to the specified location.

In still a further aspect of the present invention, a user interface for communicating whether one or more users are assigned to a specified healthcare testing location is provided. The user interface includes a first screen area having means for adding or removing one or more users from a healthcare testing location and a second screen having means for indicating that one or more users have been successfully added or removed from the healthcare testing location.

In yet a further aspect of the present invention, a user interface for communicating whether a request to enter test results for a patient order has been authorized is provided. The user interface includes a first screen having means to identify a patient order and to enter test results for the order. The user interface also includes a second screen having means to indicate whether access to the identified patient's order is allowed.

BRIEF DESCRIPTION OF SEVERAL VIEWS OF THE DRAWINGS

The present invention is described in detail below with reference to the attached drawing figures, wherein.

DETAILED DESCRIPTION OF THE INVENTION

Figure 1:
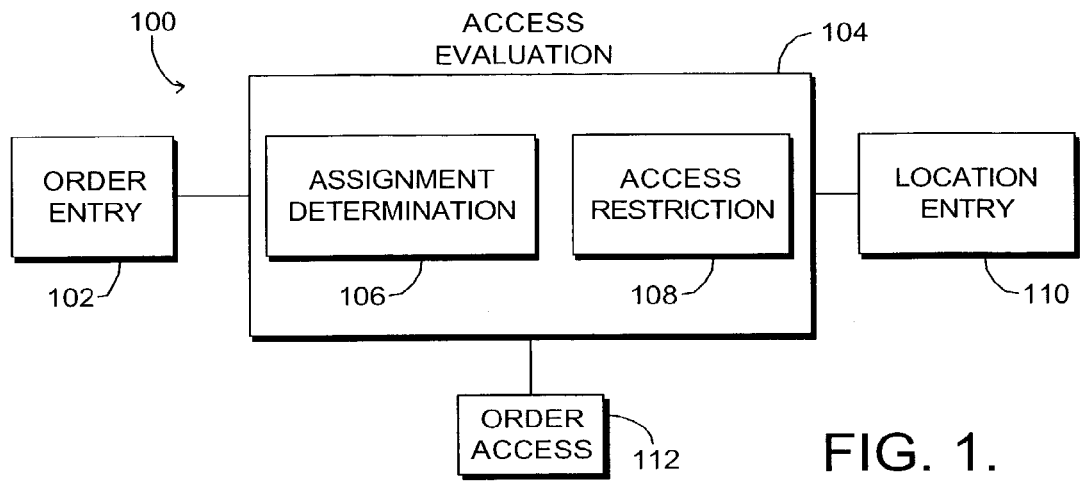
FIG. 1 is a block diagram of a computing system environment suitable for use in implementing the present invention.

The present invention is directed to a system and method for providing restricted access to patient healthcare information by determining whether one or more users are assigned to the location where the order is to be performed. FIG. 1 depicts an exemplary computer system 100 for providing restricted access to patient healthcare information. The system 100 includes an order entry module 102 coupled with an access evaluation module 104. The access evaluation module 104 includes an assignment determination sub-module 106 that determines whether one or more users are assigned to the location where the order is to be performed. The access evaluation module 104 also includes a restricted access sub-module 108 for allowing restricted access to one or more users assigned to the location where the order is to be completed. The system also includes a location entry module 110 for input of location(s) where user(s) are assigned to perform work. Finally, the system includes an order access module 112 for user(s) to access patient orders.

Those skilled in the art will appreciate that the present invention contemplates the presence of additional modules and/or sub-modules of the computer system 100, and the modules and/or sub-modules may be combined with one another and/or separated into new modules or sub-modules.

The present invention may be implemented in a variety of computing system environments. For example, each of the modules and sub-modules of the computer system 100 may be embodied in an application program running on one or more personal computers (PCs). This computing system environment is only one example of a suitable computing environment and is not intended to suggest any limitation as to the scope of use or functionality of the invention. The invention may also be implemented with numerous other general purpose or special purpose computing system environments or configurations. Examples of other well-known computing systems, environments, and/or configurations that may be suitable for use with the invention include, but are not limited to, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may be described in the general context of computer-executable instructions, such as program modules. Generally, program modules include routines, programs, objects, components, segments, schemas, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Computers typically include a variety of computer-readable media. Computer-readable media includes any media that can be accessed by a computer and includes both volatile and nonvolatile media, removable and non-removable media. By way of example, and not limitation, computer-readable media may comprise computer-storage media and communications media. Computer-storage media includes volatile and nonvolatile, removable and non-removable media implemented in any method or technology for storage of information such as computer-readable instructions, data structures, program modules, or other data. Computer-storage media include, but is not limited to, RAM, ROM, EEPROM, flash memory or other memory technology, CD-ROM, digital versatile disks (DVD), holographic or other optical storage, magnetic cassettes, magnetic tape, magnetic disk storage or other magnetic storage devices, or any other medium which can be used to store the desired information and which can be accessed by a computer.

Communications media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communications media includes wired media such as a wired network or direct wired connection, and wireless media such as acoustic, RF, infrared, spread spectrum and other wireless media. Communications media are commonly used to upload and download information in a network environment, such as the Internet. Combinations of any of the above should also be included within the scope of computer-readable media.

The computer may operate in a networked environment using logical connections to one or more remote computers, such as a personal computer, a server, a router, a network PC, a peer device or other common network node, and typically includes many or all of the elements described above. The logical connections may include connections to a local area network (LAN), a wide area network (WAN), and/or other networks. Such networking environments are commonplace in offices, enterprise-wide computer networks, intranets, and the Internet.

Computer-storage mechanisms and associated media provide storage of computer-readable instructions, data structures, program modules, and other data for the computer. A user may enter commands and information into the computer through input devices such as a keyboard and pointing device, commonly referred to as a mouse, trackball or touch pad. Other input devices may include a microphone, touchscreen, camera, joystick, game pad, scanner, or the like. In addition to a monitor or other type of display device, computers may also include other peripheral output devices such as speakers and printers, which may be connected through an output peripheral interface.

Although many other internal components of computers have not been discussed herein, those of ordinary skill in the art will appreciate that such components and their interconnection are well known. Accordingly, additional details concerning the internal construction of computers need not be disclosed in connection with the present invention.

The present invention is particularly suited for use in the healthcare industry. Examples of unified and integrated database applications for storing patient orders include, but are not limited to, the HNA Classic™ and Cerner Millennium™ systems marketed and sold by Cerner Corporation of Kansas City, Mo.

In a healthcare setting, a physician or other healthcare provider orders one or more healthcare testing procedures for a patient including, but not limited to, a breast mammography, Pap smear, complete blood count, pregnancy tests, and glucose monitoring. The order for the patient is assigned to a specified location for completion. In a large healthcare organization, there may be multiple locations that can complete the order. One of skill in the art will realize that an order may be assigned to a specified location for a variety of reasons. For example, an order may be assigned based on information regarding the patient (i.e., adult vs. pediatric patient) or based on available users to complete the order.

Further, an order may be assigned to a specified location in a variety of ways. For example, a physician may order tests to be performed on a specimen taken from a patient. When assigning the order to a specified location, the system may route the patient's entire specimen to a specified location or the patient's specimen, such as blood, may be divided and the subdivided portions of the specimen may be assigned to different locations. The order also may be assigned to a specified location by placing the order in a work queue or by specifying the patient examination room where patient testing, such as radiology, is to be performed. In other words, the specified location where an order may be performed may be a physical workstation, such as an instrument, workbench, service resource, surgical suite, or patient examination room, or a virtual location, such as a work queue comprising a series of testing requests.

Figure 2:
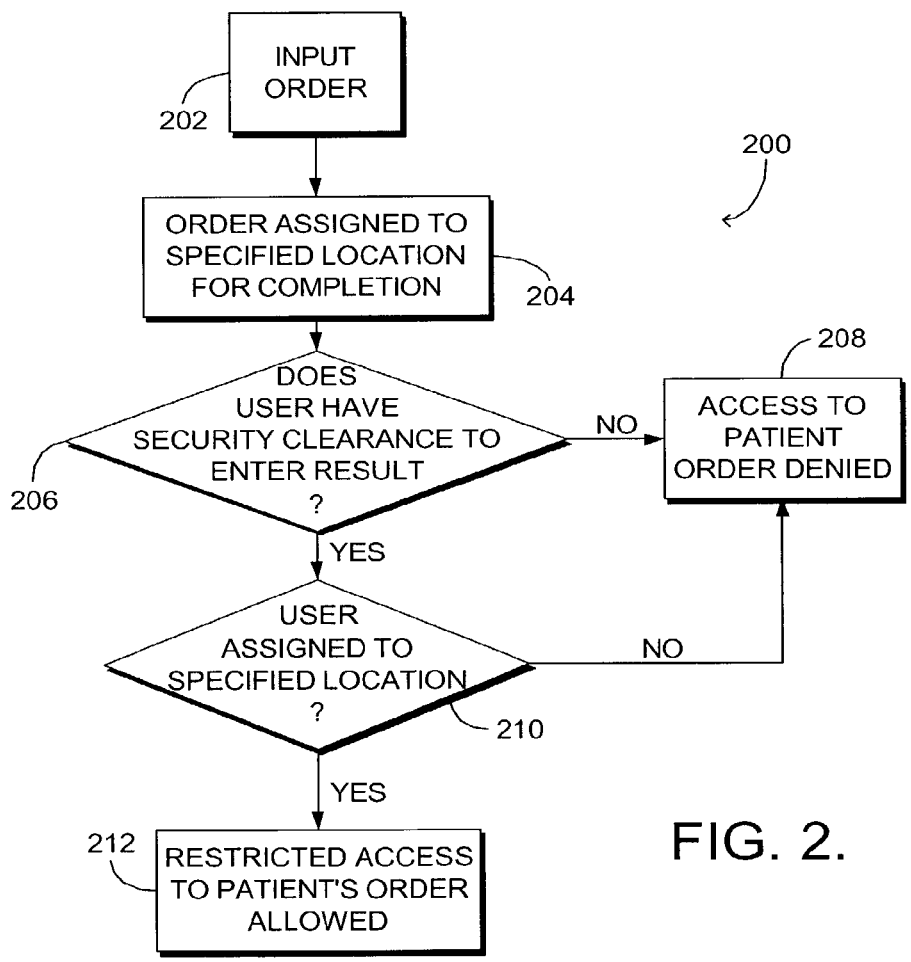
FIG. 2 is a flowchart representative of a computer program for providing restricted access to patient healthcare information in accordance with an embodiment of the present invention.

Referring next to FIG. 2, a flow diagram 200 is provided which illustrates an embodiment for providing user(s) restricted access to patient orders in accordance with the present invention. An order is input at block 202 and assigned to a specified location at block 204. Alternatively, the order may be assigned to a specified location prior to being input into the system. At decision block 206, it is determined whether the user seeking access to an order has security clearance to enter the necessary results for that type of order. For example, a particular user may enter general toxicology results but does not have security clearance to enter forensic toxicology results. If the user does not have security clearance to enter results for the type of order, restricted access to the patient order is denied at block 208. If the user has security clearance to enter results for the type of order, the system continues to decision block 210. In an alternative embodiment in which security clearance is assumed, decision block 206 is bypassed.

At block 210, the system determines whether the user seeking access is assigned to the location where the order is to be performed. If not, access to the patient order is denied at block 208. If the system determines the user is assigned to the location where the patient order is to be performed at block 210, then restricted access to the patient's order is granted at block 212. In addition to the patient's order, the system also may provide restricted access to additional health information for the patient.

By way of example, a blood specimen is taken from a patient and the patient's physician orders a complete blood count test to be performed on the specimen. The order is input at block 202. The order is assigned to the Automated Cell Count service resource in the Automated Hematology Sub Section of the Hematology Department of a healthcare organization. A user may seek access to the patient's order in a variety of ways including, but not limited to, selecting an order from a list or by entering an identification value that represents an order, patient, or specimen. When a user seeks access to one or more patient orders, the user may be identified in a variety of ways including, but not limited to, entering an identification value into the system that represents the user.

Figure 3:
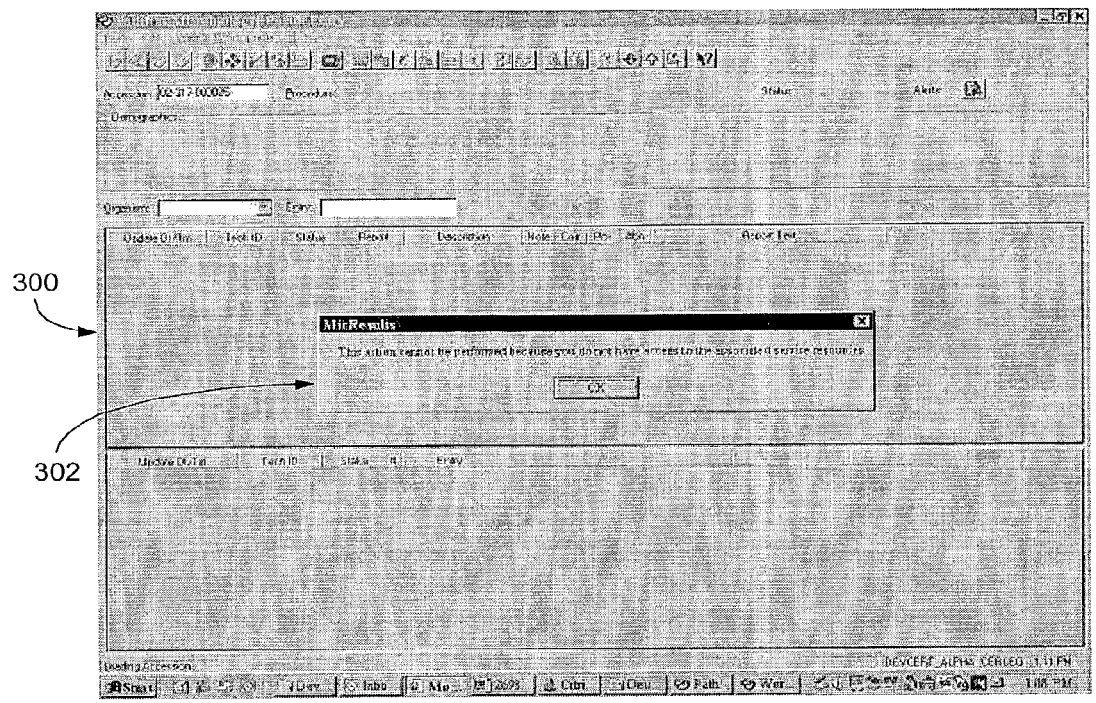
FIG. 3 is a screen shot illustrating an exemplary implementation for result entry wherein access to a patient's order has been denied.

In the illustrated embodiment, the system determines that the user is allowed to enter results for complete blood counts at decision block 206. Then at decision block 208, the system determines whether the user is assigned to the Automated Cell Count service resource in the Automated Hematology Sub-Section of the Hematology Department of the healthcare organization. If the user is assigned to that testing location, the system grants the user restricted access to the patient's order so that the user may enter results for the complete blood count test of the order. If the user is not assigned to that testing location, access to the patient's order is denied. With reference to FIG. 3, an exemplary result entry screen 300 is shown. The result entry screen 300 shows that the user is denied access to the patient's order in field 302 because they are not assigned to the testing (or service) location where the order is to be performed.

Figure 4:
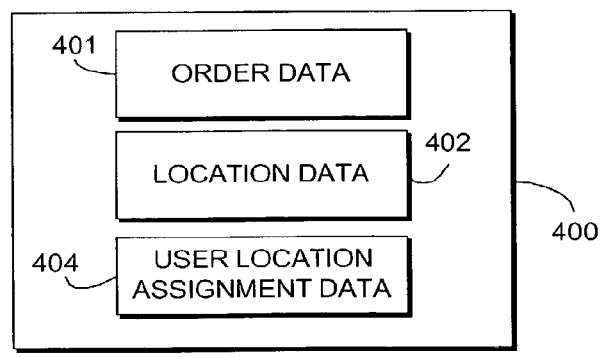
FIG. 4 is a block diagram of a data structure in accordance with an embodiment of the present invention.

Turning now to FIG. 4, an exemplary data structure 400 is shown in accordance with an embodiment of the present invention. The data structure 400 includes a field 401 that contains data indicative of the order to be completed, a field 402 that contains data indicative of the specified location at which a healthcare related order is to be performed and a field 404 indicative of the location assignment data of one or more users so that restricted access may be granted to one or more users assigned to the specified location. As is well known in the art, the data structure 400 may be stored on one or more computer-readable media, and the data structure 400 may contain additional fields.

Figure 5:
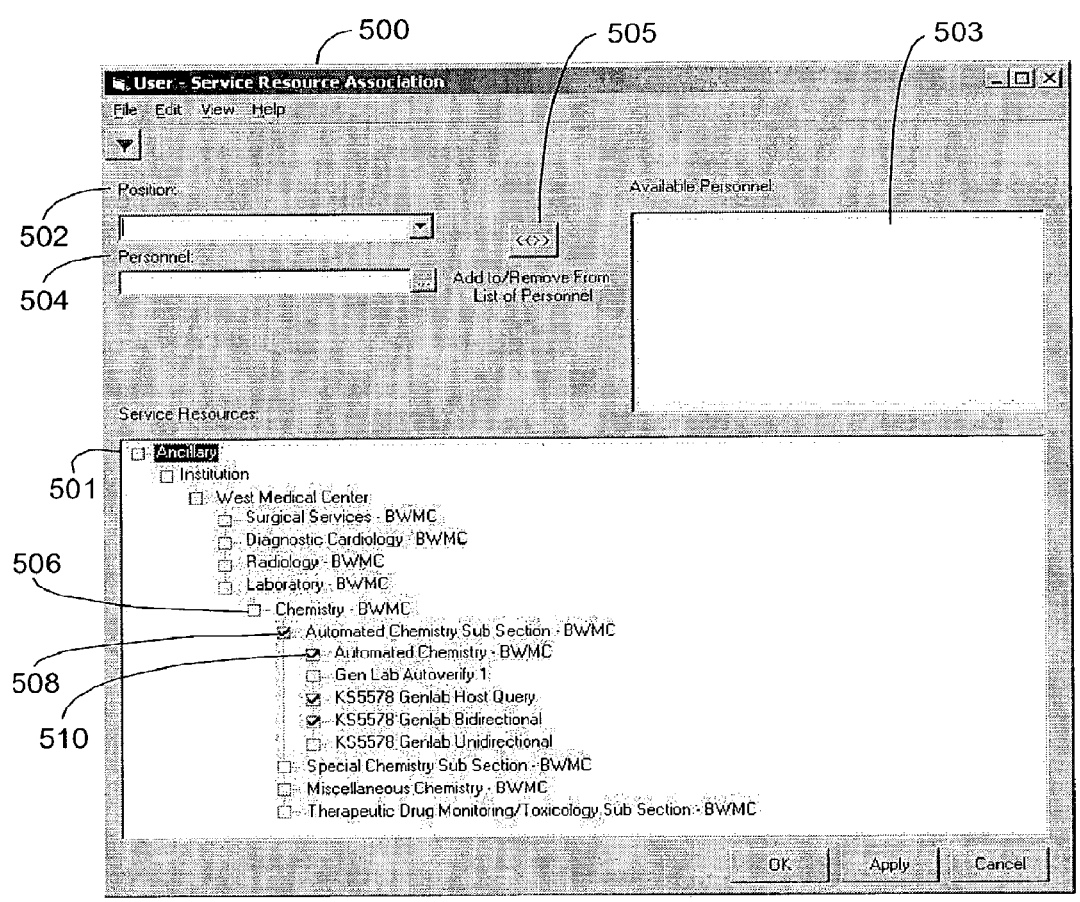
FIG. 5 is a screen shot illustrating an exemplary implementation for entry of user work location information.

Referring now to FIG. 5, an exemplary screen shot illustrating the association of location(s) with user(s) is depicted. FIG. 5 depicts an exemplary build tool display 500 used to input the location(s) where user(s) are authorized to perform testing procedures. The tool provides the ability to add and/or remove user(s) to or from one or more locations. In the illustrated example, testing locations are listed in field 501. The locations listed in the menu include, but are not limited to, departments 506, sub-departments 508 and service resources 510. One of ordinary skill in the art will realize that locations may be indicated in a variety of ways.

In the illustrated example, one or more testing locations are selected from the menu by checking the box for the one or more desired location(s). Test locations may be removed by unchecking the box. Personnel/users authorized to perform tests at the selected location(s) are listed in field 503. One or more users may be added or removed from those authorized to perform tests at the selected location(s) by identifying the desired position in field 502 and clicking button 505. One or more users may also be added or removed from those authorized to perform tests at the selected location(s) by identifying the particular user in personnel field 504 and clicking button 505. The system will then present an indicator that one or more users have been added or removed from the selected location(s). One of skill in the art will realize that there are a number of ways to indicate that a user has been added or removed from a location(s). In the illustrated embodiment, users who are added to the selected location(s) are listed in field 503. Users who are removed from the selected location(s) are removed from field 503.

One of ordinary skill in the art will appreciate the present invention provides a system and method for allowing restricted access to patient healthcare information. The present invention determines whether one or more users are assigned to the location where an order for a patient is to be performed and, if so, allows those users restricted access to the order. The system may include an order entry module, an access evaluation module, a location entry module and an order access module. The access evaluation module may include a location determination sub-module for determining whether one or more users are assigned to the specified location where an order for a patient is to be performed and a restricted access sub-module coupled with the location determination module and configured to allow restricted access to one or more users assigned to the specified location.

Alternative embodiments and implementations of the present invention will become apparent to those skilled in the art to which it pertains upon review of the specification, including the drawing figures. Accordingly, the scope of the present invention is defined by the appended claims rather than the foregoing description.

We claim:

1. A computer-implemented method, which is carried out using one or more of a processor and computer-storage media, for allowing restricted access to a patient's healthcare information in a computing environment of a healthcare organization, the method comprising:
   receiving an order specifying a healthcare procedure to be performed on a patient;
   receiving a location assignment that assigns the order to be performed at a healthcare-service location;
   receiving from a user a request to access the order;
   determining by the processor that the user is assigned to the healthcare-service location at which the order is assigned to be performed; and
   allowing the user to access the order based on the user being assigned to the healthcare-service location at which the order is assigned to be performed.

2. The method of claim 1, further comprising:
   allowing the user assigned to the healthcare-service location to access other healthcare information of the patient.

3. The method of claim 1, further comprising:
   determining that the user has security clearance to enter test results of the order to which the user seeks access.

4. The method of claim 3, wherein the healthcare-service location at which the order is to be performed is either a physical location or a virtual location.

5. The method of claim 4, wherein the healthcare-service location is a work queue.

6. The method of claim 4, wherein the healthcare-service location is a patient examination room.

7. The method of claim 4, wherein the order comprises analyzing a specimen collected from the patient and wherein the healthcare-service location is a testing laboratory at which the specimen is analyzed.

8. The method of claim 4, wherein the healthcare-service location is a surgical suite.

9. The method of claim 3, further comprising:
   allowing the user to input test results of the order.

10. A computer system embodied on one or more non-transitory computer storage media having computer-executable instructions embodied thereon for allowing restricted access to patient healthcare information, the system comprising:
    a location-entry module that receives input indicating a healthcare location to which a user is assigned;
    an order-entry module that receives input indicating an order, which specifies a healthcare procedure to be performed on a patient, wherein the order is assigned to the healthcare location at which the order is to be performed;
    an assignment-determination module that determines the user is assigned to the healthcare location, at which the order is to be performed, when a request is received to allow the user to access the order; and
    a restricted-access module that is communicatively coupled with the assignment-determination module and that provides to the user restricted access to the order based on the user being assigned to the healthcare location at which the order is to be performed.

11. The system of claim 10,
    wherein the location-entry module receives input via a user interface, and
    wherein the user interface includes:
       a first portion depicting the healthcare location that is usable to perform the order, and
       a second portion depicting, in response to selection of the healthcare location, a list of personnel that are authorized to perform the order at the healthcare location.

12. The system of claim 11, wherein the assignment-determination module determines that the user is assigned by referencing the list of personnel.

13. The system of claim 10, wherein the restricted-access module is configured to restrict access of the user to a second order, which is not assigned to the healthcare location.

14. The system of claim 10, wherein the healthcare location includes a patient examination room, a testing laboratory, or a surgical suite.

15. One or more non-transitory computer-readable media having stored thereon computer-executable instructions that, when executed, cause a computing device to perform a method of controlling access to sensitive information, the method comprising:
    receiving an order specifying a healthcare procedure to be performed on a patient;
    receiving a location assignment that assigns the order to be performed at a healthcare-service location;
    receiving from a user a request to access the order;
    determining by the processor that the user is assigned to the healthcare-service location at which the order is assigned to be performed; and
    allowing the user to access the order based on the user being assigned to the healthcare-service location at which the order is assigned to be performed.

16. The method of claim 15, further comprising:
    allowing the user to input test results of the order.

17. The method of claim 15, further comprising:
    allowing the user assigned to the healthcare location to access other healthcare information of the patient.

* * * * *